(12) United States Patent
Henry et al.

(10) Patent No.: US 7,049,474 B1
(45) Date of Patent: May 23, 2006

(54) WATER DILUTED CUMENE HYDROPEROXIDE SOLUTIONS

(75) Inventors: Keith E. Henry, Allison Park, PA (US); John E. Aiken, Monroeville, PA (US)

(73) Assignee: Sunoco, Inc. (R&M), Philadelphia, PA (US)

( * ) Notice: Subject to any disclaimer, the term of this patent is extended or adjusted under 35 U.S.C. 154(b) by 0 days.

(21) Appl. No.: 09/660,099

(22) Filed: Sep. 12, 2000

(51) Int. Cl.
*C07C 409/10* (2006.01)

(52) U.S. Cl. ...................................... 568/568; 568/576

(58) Field of Classification Search ............... 568/568, 568/576, 571
See application file for complete search history.

(56) References Cited

U.S. PATENT DOCUMENTS

| | | |
|---|---|---|
| 2,547,938 A | 4/1951 | Hall et al. |
| 2,706,708 A | 4/1955 | Frank et al. |
| 2,722,506 A | 11/1955 | Ellis |
| 2,735,871 A | 2/1956 | Smith |
| 3,049,477 A | 8/1962 | Cooke |
| 3,092,587 A | 6/1963 | Ester et al. |
| 3,519,690 A | 7/1970 | Joris et al. |
| 3,773,687 A | 11/1973 | Borchert et al. |
| 4,316,767 A | 2/1982 | Saida et al. |
| 4,654,124 A | 3/1987 | Elias et al. |
| 5,202,498 A * | 4/1993 | Elias .......................... 568/559 |

OTHER PUBLICATIONS

CA:87:200365 abs of Zh. Fiz. Khim. by Markaryan et al 51(9) pp. 2385-2387 1977.*

* cited by examiner

*Primary Examiner*—Brian Davis
(74) *Attorney, Agent, or Firm*—Robert A. Koons, Jr.; Matthew P. McWilliams; Drinker Biddle & Reath LLP

(57) ABSTRACT

The present invention provides for the use of water, rather than cumene, as a more environmentally acceptable diluent for purified cumene hydroperoxide (CHP) solutions. From 1 to about 6 weight percent water can be used to dilute purified CHP solutions, thus reducing or eliminating the use of a hazardous compound, cumene, as a diluent. The method and CHP-water solutions of the present invention should significantly reduce or eliminate the hazardous emissions problems encountered with the use of cumene as a diluent and make CHP solutions more environmentally acceptable to produce, transport and use. Water as a diluent also depresses the freezing point of the resultant solution, thereby permitting year-round use of higher concentration CHP solutions. Water diluted CHP solutions will also reduce cumene-related impurities in finished products made therefrom.

14 Claims, 4 Drawing Sheets

WATER DILUTED CUMENE HYDROPEROXIDE SOLUTIONS

FIELD OF INVENTION

This invention relates in general to methods of reducing hazardous air pollutants in cumene hydroperoxide and improving the shipping and handling of cumene hydroperoxide in cold weather and more specifically, to the partial or total replacement of cumene as a diluent by water.

BACKGROUND OF THE INVENTION

Cumene hydroperoxide (CHP) is produced as an intermediate product in the manufacture of phenol from cumene and oxygen. In the BP Chemicals/Hercules and similar phenol processes, cumene is oxidized to CHP which can then be cleaved with sulfuric acid to yield phenol and acetone. These processes account for nearly all the phenol produced in the world today and are described in numerous patents and published literature dating back to the early 1950's. CHP synthesis yields small amounts of the following which are considered impurities: cumene, α-methylstyrene (AMS), dimethyl benzyl alcohol (DMBA) and acetophenone (AP). Further processing steps such as those described in U.S. Pat. No. 4,654,124, assigned to the same assignee as the present invention and incorporated in its entirety herein by reference, are necessary to remove these impurities and color formers from the CHP. Such purification as by the methods of the '124 patent may result in a CHP solution with a purity of greater than 92 weight percent.

Under United States federal regulations, 90 weight percent CHP is the maximum concentration permitted for domestic transport (49 C.F.R., Sec. 173.225, Organic Peroxide Table-revised Oct. 1, 1998). Therefore, refined CHP must be diluted, typically with cumene, to a concentration of 82 weight percent-90 weight percent to produce commercial grades of CHP that can be transported in compliance with these regulations.

The use of cumene as a diluent of CHP solutions presents several problems for CHP producers, transporters and end users. First, because the U.S. Clean Air Act Amendments (Public Law 101–549 Sect. 112(b)) classify the diluent, cumene, as a hazardous air pollutant, precautions must be taken when producing, transporting and using CHP solutions to minimize cumene emissions. Second, because cumene can be considered an impurity in CHP solutions, it may have to be removed by the end user, thereby creating additional hazardous emissions problems. Third, if the cumene added to CHP solutions is not removed, it can result in the end user's finished product containing unacceptable impurities. Fourth, the climatic conditions at the end user's facility may vary and necessitate changing the concentration of purified CHP utilized. A lower concentration CHP solution, i.e., higher cumene, typically is used to prevent the CHP solution from freezing in colder months, but a higher concentration CHP solution, i.e., lower cumene, is used in warmer months. Finally, the presence of cumene in CHP solutions may result in a reduced yield in the end user's process(es). The Inventors are unaware of any diluent, other than cumene, that is being used commercially with CHP.

Therefore, a need exists in the art for a CHP-diluent solution which will reduce or eliminate the hazardous emission problems associated with current CHP solutions, thus making CHP solutions more environmentally acceptable to produce, transport and use. In addition, the CHP-diluent solution should have minimal or no detrimental effects on the end user's finished product or process yield(s). The CHP-diluent solution should also preferably depress the CHP solution's freezing point to obviate the necessity of CHP users having to switch concentrations of CHP in response to changing climatic conditions at their facilities. Moreover, the diluent should have minimal effect on the viscosity of the resultant solution.

SUMMARY OF THE INVENTION

The present invention provides a method of reducing hazardous emissions from a purified cumene hydroperoxide solution by adding from 1 to 6 weight percent water to produce a mixture. The present invention further provides a method of depressing the freezing point of a purified cumene hydroperoxide solution by adding from 1 to 6 weight percent water to produce a mixture. The present invention still further provides for a composition comprising cumene hydroperoxide solution with from 1 to 6 weight percent water. The present invention yet further provides a method of preparing crude CHP solution for transport by providing crude CHP solution; purifying the crude CHP to a purity of at least 80%; producing a mixture by adding from 1 to 6 weight percent water to the purified CHP solution and placing the mixture in a transport vessel. The present invention yet still further provides a method of obviating the seasonal adjustment of CHP concentrations in transporting purified CHP solutions by adopting a standard concentration CHP solution; adding from 1 to 6 weight percent water to the standard concentration CHP solution to produce a mixture and shipping the mixture at all times of the year. These and other advantages and benefits will be apparent from the Detailed Description of the Invention herein below.

BRIEF DESCRIPTION OF THE FIGURES

The present invention will be described for the purposes of illustration, but not limitation, in conjunction with the following figures, wherein.

DETAILED DESCRIPTION OF THE INVENTION

Figure 1:
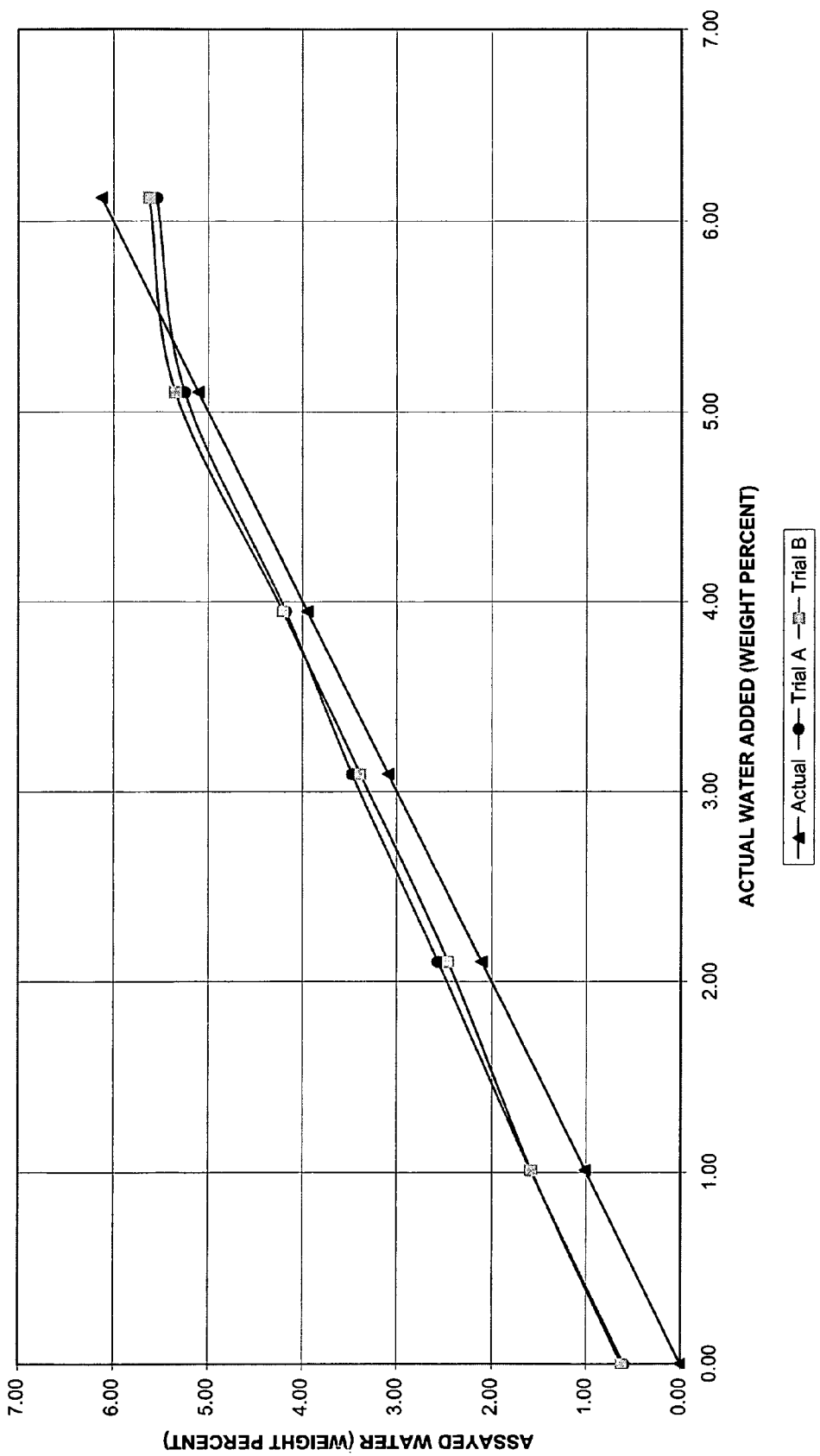
FIG. 1 illustrates a CHP-Water Assay using approximately 88% CHP.

The method of the present invention involves the use of water, from about 1 to about 6 weight percent, as a diluent for purified CHP solutions. By purified CHP solutions the inventors herein mean a solution which prior to dilution is greater than 80% CHP with the remainder being predominately dimethyl benzylalcohol and acetophenone. It most likely has undergone some purification to remove nearly all the considerably lower-boiling and the high boiling impurities.

In addition to being considered an impurity, water is generally thought, by those of ordinary skill in the art, to have little solubility in CHP and therefore of no practical significance. Contrary to this accepted wisdom, the Inventors have found that water can be added to purified CHP solutions as an alternative diluent for a portion of or all of the previously added cumene. Although it is well known that solvents tend to depress the freezing point of materials, the Inventors did not expect such a small percentage of water to so significantly depress the freezing point of CHP solutions. One of ordinary skill in the art would have expected cumene to have a greater effect than water on freezing points depression because the freezing point range of the CHP solutions is well below the freezing point of water. The freezing point of cumene itself is −96° C. Water is known to be used in the prior art as a diluent for organic substances that are highly soluble in water and have melting points well above the freezing point of water, such as phenol and neopentyl glycol.

The Inventors have found that water can be used as a diluent to reduce the CHP concentration to levels which will comply with the United States regulations for the transportation of CHP. Such use of water, rather than cumene, as a diluent provides several advantages in the resultant CHP solution. One beneficial effect of the use of water as a diluent is to reduce the hazardous emissions encountered in prior art CHP solutions because a hazardous chemical, cumene, is not added to the purified CHP solution. Another beneficial effect of water as a diluent for CHP solutions is that water will depress the freezing point of the resultant solution by as much as 15° to 20° F. (8.4 to 11.2° C.). This lowered freezing point is advantageous for several reasons.

1. A higher purity CHP solution can be utilized by end users on a year-round basis because the freezing point of the water-diluted CHP solution is lowered. This should significantly reduce or eliminate the end user's need to change CHP concentrations in response to changes in ambient temperatures at their facilities.
2. The addition of water to purified CHP solutions should also reduce cumene-related impurities in the end user's finished products
3. The addition of water to purified CHP solutions may increase process yields.
4. The suppliers of CHP-water solutions may save money by standardizing their production facilities, because they may not have to dilute purified CHP solutions to different percentages at various times of the year depending on climatic conditions at end user's facilities. In addition, the suppliers will not have to add cumene to their purified CHP solutions, thereby reducing both the environmental hazards and the productions costs associated with making CHP solutions.

Because of the limited solubility of water in CHP, an excessive amount of water added to the CHP will form a second aqueous phase in the container. Therefore, a reliable method of assaying the amount of water in the CHP phase of the solution was developed.

Water Assay for CHP

An empty bottle was weighed to obtain a tare weight. An aliquot of purified CHP, of either approximately 88% or 90% purity, was added and the bottle's weight re-determined. Subtracting the tare weight from the weight of the bottle with purified CHP yielded the net weight of purified CHP. An aliquot of water was added to the bottle. The aliquot was approximately the amount needed to produce the desired percentage of water added for the sample, i.e., 1%, 2%, etc. The bottle's weight was again determined and this weight subtracted from the weight of the bottle with purified CHP, thus yielding a net weight of water. The net weight of water was divided by the net weight of purified CHP to yield the percent water actually added. The CHP-water mixtures were shaken until clear.

One ml CHP-water samples, taken from CHP-water solutions prepared as above, were injected into a gas chromatograph (Hewlett-Packard model HP 5890) equipped with a thermal conductivity detector, and a 6 ft.×⅛ inch (182.88 cm×0.318 cm) stainless steel capillary column containing 80–100 mesh Porapack-Q® packing material manufactured by Supelco and others. The chromatograph was operated at a temperature below 220° C. with a flow rate of 20 ml/min column and 30 ml/min reference helium. A typical chromatogram shows the water peak eluting at about 2.7 minutes and the CHIP between 4.5 and 5.5 minutes. The area count is converted to a weight percent based on calibration of external standards with known amounts of water addition to acetone. For this method, the Inventors prefer to use an auto-sampler for precise and reproducible control of amount injected.

Figure 2:
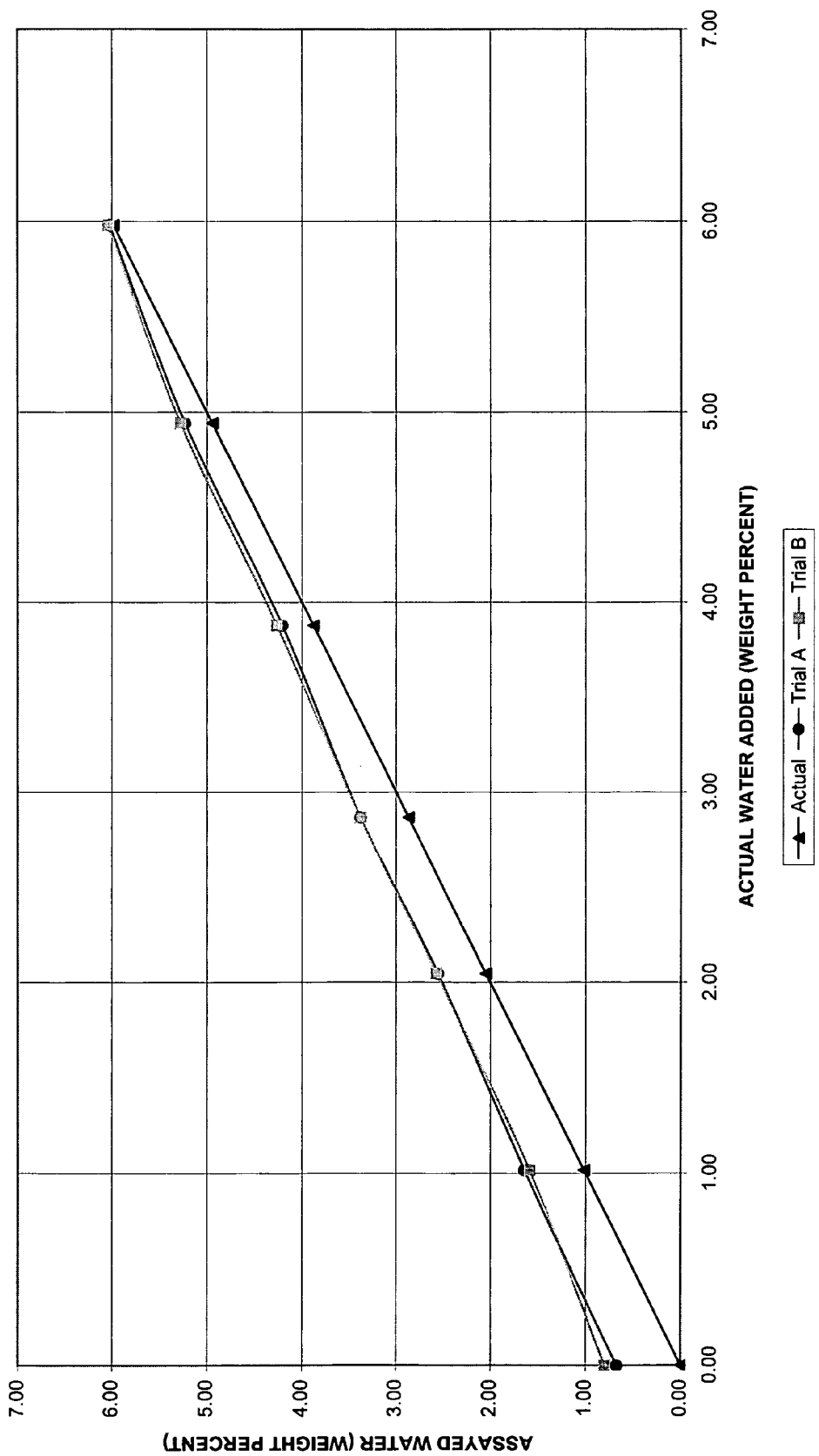
FIG. 2 illustrates a CHP-Water Assay using approximately 90% CHP.

The results of the CHP-water analysis are contained in Table 1 and illustrated in FIG. 1 for purified CHP with an approximate purity of 88% and in Table II and FIG. 2 for purified CHP with an approximate purity of 90%. Analysis of the starting material indicated that a slight amount of water was present. It will be apparent from comparing the data and looking at the figures, that this assay is accurate and reproducible because the amounts determined by both trials in this assay correlate rather well to the actual amounts of water added, less that initially present, and to each other for 88% CHP and 90% CHP. The higher concentrations of water in purified CHP solutions appear to produce a greater deviation between the actual amounts of water added and that analyzed than at lower water concentrations. Without being limited to any specific explanation for this phenomenon, the Inventors believe that it is more difficult to completely dissolve water in CHP as the solution approaches the solubility limit of water in CHP.

TABLE I

Analysis of 88% CHP + Water Samples

| Sample No. | Contents 88% CHP | Tare Wt g | Tare Wt + CHP g | Net Wt CHP g | Tare Wt + CHP + Water g | Net wt Water g | Water Added (Actual) weight percent | Water Added (Determined by CHP-water Assay) weight percent Trial A | Trial B |
|---|---|---|---|---|---|---|---|---|---|
| 1 | +0% water | 15.22 | 31.74 | 16.51 | 31.74 | 0.00 | 0.00 | 0.60 | 0.62 |
| 2 | +1% water | 14.95 | 31.02 | 16.07 | 31.19 | 0.16 | 1.01 | 1.59 | 1.58 |
| 3 | +2% water | 14.99 | 30.78 | 15.78 | 31.11 | 0.33 | 2.10 | 2.56 | 2.46 |
| 4 | +3% water | 15.19 | 30.77 | 15.57 | 31.25 | 0.48 | 3.09 | 3.47 | 3.39 |
| 5 | +4% water | 15.06 | 31.04 | 15.97 | 31.67 | 0.63 | 3.95 | 4.18 | 4.21 |
| 6 | +5% water | 15.11 | 31.39 | 16.27 | 32.22 | 0.83 | 5.10 | 5.25 | 5.34 |
| 7 | +6% water | 15.12 | 31.44 | 16.32 | 32.44 | 1.00 | 6.12 | 5.54 | 5.62 |

TABLE II

Analysis of 90% CHP + Water Samples

| Sample No. | Contents 88% CHP | Tare Wt g | Tare Wt + CHP g | Net Wt CHP g | Tare Wt + CHP + Water g | Net wt Water g | Water Added (Actual) weight percent | Water Added (Determined by CHP-water Assay) weight percent | |
|---|---|---|---|---|---|---|---|---|---|
| | | | | | | | | Trial A | Trial B |
| 1 | +0% water | 15.23 | 31.89 | 16.66 | 31.89 | 0.00 | 0.00 | 0.68 | 0.80 |
| 2 | +1% water | 15.08 | 31.63 | 16.55 | 31.80 | 0.17 | 1.02 | 1.64 | 1.59 |
| 3 | +2% water | 15.13 | 31.67 | 16.55 | 32.01 | 0.34 | 2.05 | 2.55 | 2.57 |
| 4 | +3% water | 15.10 | 31.95 | 16.85 | 32.43 | 0.48 | 2.87 | 3.38 | 3.38 |
| 5 | +4% water | 15.22 | 32.05 | 16.83 | 32.70 | 0.65 | 3.88 | 4.21 | 4.27 |
| 6 | +5% water | 15.04 | 32.52 | 17.47 | 33.38 | 0.86 | 4.94 | 5.23 | 5.28 |
| 7 | +6% water | 15.17 | 32.42 | 17.26 | 33.46 | 1.03 | 5.98 | 6.02 | 6.04 |

Freezing Point Test

The effect of water as a diluent on the freezing point of various CHP-water solutions was determined and the results are summarized in Table III. Briefly, production samples of CHP diluted with from 1 weight percent to 6 weight percent water were frozen in a Thermotron® cooling chamber (Venturedyne Ltd., Milwaukee, Wis., USA) equipped with an internal temperature controller and an external thermocouple temperature meter. A boiling chip was added to each sample to reduce supercooling because of the difficulty in freezing small samples of CHP. The material becomes very viscous and requires a nucleating site to begin forming a white crystalline solid. All samples were cooled to about −37° F. (−38° C.). After all the samples were frozen, the cooling chamber temperature was increased in 1–2° F. (0.56–1.11° C.) increments and stabilized for a minimum of four hours. The condition of the samples was visually observed and recorded. Table III lists the temperature at which the sample appeared to contain only liquid, i.e., the melting or freezing point. Assessment of the samples containing 5% and 6% water was complicated by the fact that some of the water formed a separate phase which then froze into ice crystals on the side of the vial. These ice crystals made it difficult to determine exactly when the rest of the liquid was completely melted. The data in the table are the best estimates of when essentially all of the liquid had melted.

TABLE III

Melting Point for Various CHP-Water Solutions
Temperature at Which Sample First Appeared to all Liquid

| Wt. % H₂O | 20 ml Bottles | | 1 ml Vials | | 1 ml Vials | | 20 ml Vial |
|---|---|---|---|---|---|---|---|
| | 88% CHP °F. (°C.) | 90% CHP °F. (°C.) | 88%- Trial A °F. (°C.) | 88%- Trial B °F. (°C.) | 90%- Trial A °F. (°C.) | 90%- Trial B °F. (°C.) | 91.9% CHP °F. (°C.) |
| 0 | +1.0 (−17.2) | +6.3 (−14.3) | −3.7 (−19.8) | −3.7 (−19.8) | −2.2 (−19.0) | −2.2 (−19.0) | |
| 1 | −9.0 (−22.8) | −2.2 (−19.0) | −11.0 (−23.9) | −11.0 (−23.9) | −11.0 (−23.9) | −11.0 (−23.9) | |
| 2 | −16.0 (−26.7) | −11.0 (−23.9) | −17.0 (−27.2) | −17.0 (−27.2) | # | # | +2.2 (−16.6) |
| 3 | −16.0 (−26.7) | −17.0 (−27.2) | −16.0 (26.7) | −16.0 (−26.7) | −17.7 (−27.6) | −17.7 (−27.6) | −1.2 (−18.4) |
| 4 | −2.2 (−19.0) | −2.2* (−19.0) | −9.0 (−22.8) | −9.0 (−22.8) | −9.0 (−22.8) | −9.0 (−22.8) | −3.0 (−19.4) |
| 5 | −2.2* (−19.0) | −2.2* (−19.0) | 11.7* (−11.3) | 11.7* (−11.3) | 6.3* (−14.3) | 6.3* (−14.3) | |
| 6 | −2.2* (−19.0) | −2.2* (−19.0) | 11.7* (−11.3) | 11.7* (−11.3) | 14.6* (−9.7) | 14.6* (−9.7) | |

Never froze
*Essentially all liquid, some ice crystals on container's inside wall up to 32° F., 0° C.

Figure 3:
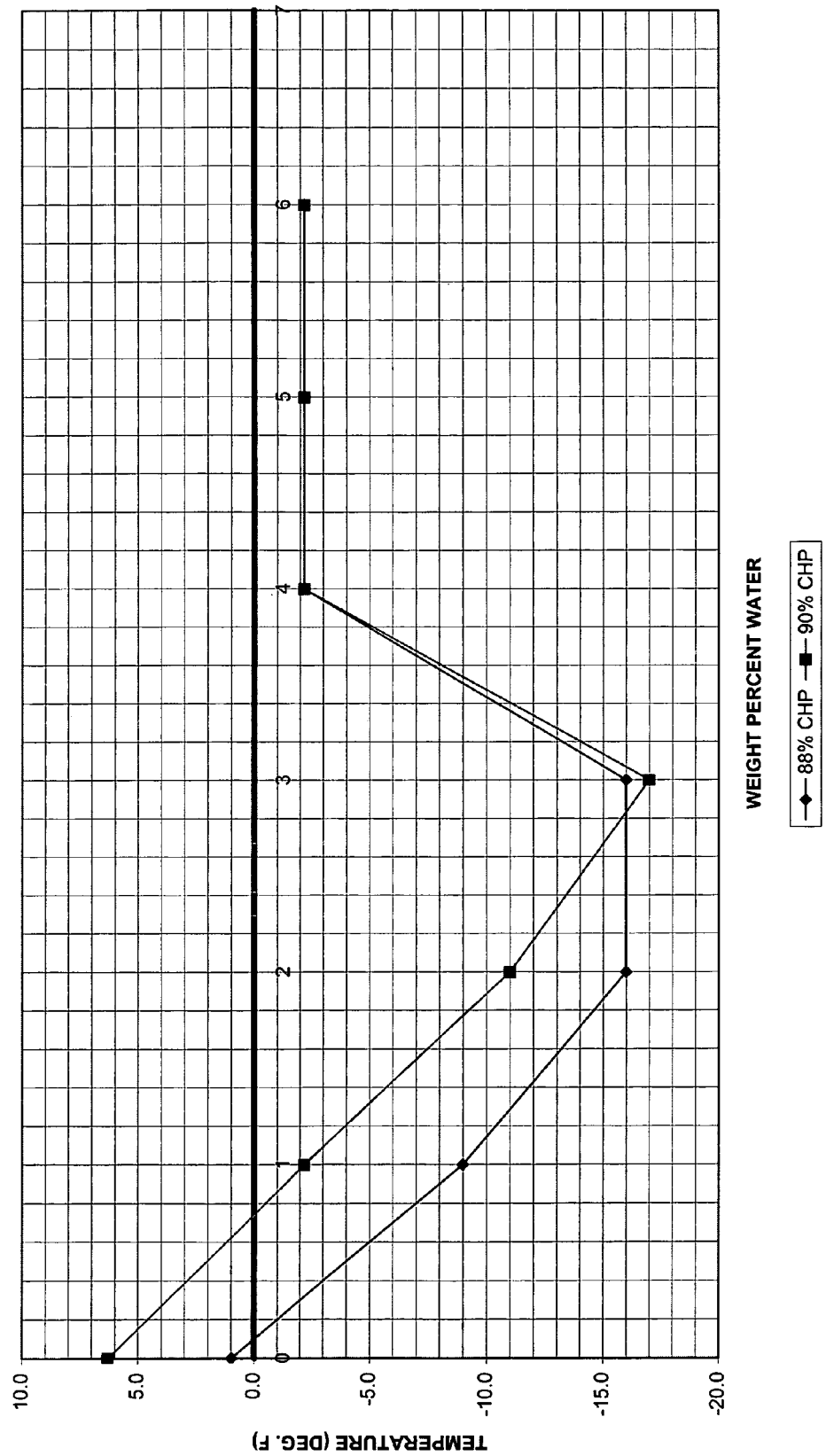
FIG. 3 illustrates freezing point depression data for various CHP-water blends.

In the interest of clarity, only data from the experiments conducted using 20 ml bottles are shown in FIG. 3. As can be seen from the data in Table III and by reference to FIG. 3, the greatest freezing point depression of both 88% and 90% purity CHP solutions occurs with the use of between 2 to 3 weight percent water as a diluent. It will be seen from comparison of this data with data obtained by using 1 ml vials at each purity of CHP solution that the maximum freezing point depression is consistently observed with the use of between 2 to 3 weight percent water as a diluent. In Table III, the addition of 2% cumene in 90% CHP lowered the melt point from +6.3° F. (−14.3° C.) to +1.0° F. (−17.2° C.) while adding 2% water lowered the melt point from +6.3° F. (−14.3° C.) to −11.0° F. (−23.9° C.), thus demonstrating the unexpected superiority of water over cumene at lowering the freezing point.

Viscosity Test

Because the viscosity of the CHP-water solution at lower temperatures may have an effect on its suitability for end users, the viscosity of CHP-water solutions at various temperatures was determined by the following test.

A beaker with a 500 ml CHP-water sample was cooled in an acetone/dry ice bath. As the sample warmed, the viscosity was measured with a Brookfield™ LVT Viscometer with a No. 1 or No. 2 spindle at two speeds between 12 and 60 rpm. The viscosity in centipoise (cp) at two speeds was averaged and recorded. The temperatures were measured with a thermocouple and a meter. Temperatures were not exact as there was a constant drift upward in temperature; the average over the measuring period for that sample was reported.

Figure 4:
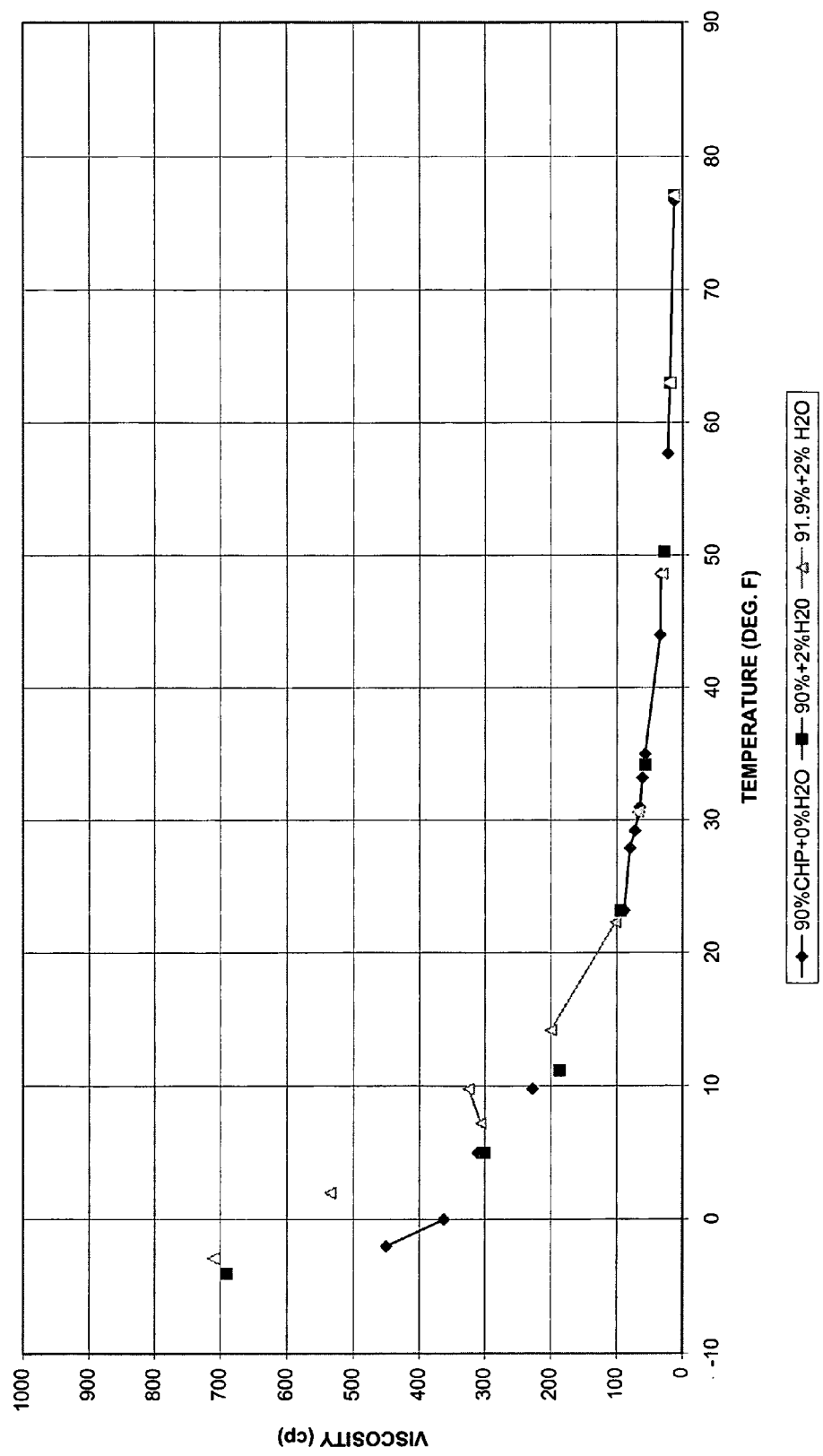
FIG. 4 illustrates viscosity of CHP-water solutions at various temperatures.

The results are contained in Table IV, and are illustrated in FIG. 4. As will be apparent from a review of Table IV and FIG. 4, the addition of 2 weight percent water to an approximately 90% purity CHP solution appears to have very little effect on viscosity over the temperature ranges assayed. The addition of 2 weight percent water as a diluent of 91.9% purity CHP does slightly increase viscosity of the solution at lower temperatures over the viscosity seen in 90% CHP alone or 90%+2 weight percent water.

TABLE IV

CHP-Water Solutions Viscosity Measurements

| Temp °F. (°C.) | 90% CHP + 0 weight percent Water Viscosity (cp) | 90% CHP + 2 weight percent Water Viscosity (cp) | 91.9% CHP + 2 weight percent Water Viscosity (cp) |
|---|---|---|---|
| 77.1 (25.1) | | 13.0 | 13.1 |
| 76.7 (24.8) | 13.2 | | |
| 63.0 (17.2) | 19.6 | 19.0 | 20.3 |
| 57.7 (14.3) | 22.5 | | |
| 50.3 (10.2) | | 28.0 | |
| 48.6 (9.2) | 33.6 | | 31.4 |
| 44.0 (6.7) | 34.5 | | |
| 35.0 (1.7) | 57.5 | | |
| 34.2 (1.2) | | 57.0 | |
| 33.2 (0.7) | 61.5 | | |
| 31.0 (−0.6) | 65.3 | | |
| 30.6 (−0.8) | 67.0 | 68.5 | |
| 29.2 (−1.6) | 73.0 | | |
| 27.9 (−2.3) | 80.2 | | |
| 23.2 (−4.9) | 88.8 | 94.0 | |
| 22.3 (−5.4) | | | 102.5 |
| 14.2 (−9.9) | | | 199.8 |
| 11.2 (−11.6) | | 190.0 | |
| 9.8 (−12.3) | 227.5 | | 325.0 |
| 7.2 (−13.8) | | | 306.0 |
| 5.0 (−15.0) | 311.0 | 300.0 | |
| 2.0 (−16.7) | | | 535.0 |
| 0.0 (−17.8) | 363.0 | | |
| −2.0 (−18.9) | 450.0 | | |
| −2.9 (−19.4) | | | 710.0 |
| −4.0 (−20.0) | | 690.0 | |

Although the description of the invention herein utilized small bottles, the Inventors contemplate the use of much larger vessels on a commercial scale, including but not limited to, large tanks for adding water to the purified CHP solutions and drums, tank trucks, tank cars or pipelines for transporting the CHP-water mixtures to end users.

The foregoing illustrations of embodiments of the present invention are offered for the purposes of illustration and not limitation. It will be readily apparent to those skilled in the art that the embodiments described herein may be modified or revised in various ways without departing from the spirit and scope of the invention. The scope of the invention is to be measured by the appended claims.

We claim:

1. A method of reducing hazardous emissions from a purified cumene hydroperoxide (CHP) solution, said method comprising diluting said purified CHP solution with x weight percent water to produce a mixture;
   wherein $1 \leq x \leq 6$.

2. The method of claim 1 further including mixing said CHP-water mixture.

3. The method of claim 1 further including transporting said CHP-water mixture.

4. The method of claim 1, wherein $2 \leq x \leq 3$.

5. The method of claim 1, wherein said purified CHP solution is at least 80% CHP.

6. The method of claim 1, wherein said purified CHP solution is at least 88% CHP.

7. The method of claim 1, wherein said purified CHP solution is at least 90% CHP.

8. A method of depressing the freezing point of a purified cumene hydroperoxide (CHP) solution, said method comprising diluting said purified CHP solution with x weight percent water to produce a CHP mixture;
   wherein $1 \leq x \leq 4$.

9. The method of claim 8 further including mixing said CHP-water mixture.

10. The method of claim 8 further including transporting said CHP-water mixture.

11. The method of claim 1, wherein $2 \leq x \leq 3$.

12. The method of claim 1, wherein said purified CHP solution is at least 80% CHP.

13. The method of claim 1, wherein said purified CHP solution is at least 88% CHP.

14. The method of claim 1, wherein said purified CHP solution is at least 90% CHP.

* * * * *